United States Patent [19]

Frankena

[11] Patent Number: 4,785,190
[45] Date of Patent: Nov. 15, 1988

[54] IRRADIATION DEVICE

[75] Inventor: Johannes A. Frankena, Drachten, Netherlands

[73] Assignee: U.S. Philips Corporation, New York, N.Y.

[21] Appl. No.: 106,480

[22] Filed: Oct. 7, 1987

[30] Foreign Application Priority Data

Oct. 15, 1986 [NL] Netherlands .......................... 8602584

[51] Int. Cl.$^4$ .............................................. G21K 5/00
[52] U.S. Cl. .............................. 250/503.1; 250/504 R; 403/93; 403/97; 362/427; 248/284; 248/291; 248/242
[58] Field of Search ........................ 250/504 R, 503.1; 403/93, 97; 362/427; 248/284, 291, 242

[56] References Cited

U.S. PATENT DOCUMENTS 4,196,354  4/1980  Wolff ................................... 250/504
4,722,502  2/1988  Mueller et al. ....................... 248/284

Primary Examiner—Bruce C. Anderson
Assistant Examiner—Jack I. Berman
Attorney, Agent, or Firm—Ernestine C. Bartlett

[57] ABSTRACT

Irradiation device having a housing (1) accommodating at least one UV-radiation source, which housing is secured by means of pivots (6) to suspension members (2, 3), each pivot being composed of two co-operating concentric rings (7,8) whose facing walls are provided with series of regularly spaced co-operating projections (11a, 11b, 11c) and recesses (12), enabling the housing to be fixed in given positions with respect to the suspension members.

3 Claims, 2 Drawing Sheets

IRRADIATION DEVICE

FIELD OF THE INVENTION

The invention relates to an irradiation device having a housing accommodating at least one radiation source, which housing is pivotably secured to suspension members on two sides located substantially opposite each other, and which housing can be fixed in given positions with respect to the suspension members. A device of this type is known from German Patent Specification No. 1,157,716.

BACKGROUND OF THE INVENTION

The known device has a comparatively small metal housing for a radiation source which can emit infrared or ultraviolet radiation. The housing is secured by means of pivots between the free ends of a resilient supporting member. The pivot has a cylindrical part secured to the supporting member, which part is pressed against a recess co-operating therewith in the housing so that the housing is resistably rotatable with respect to the member. The user can easily adjust the housing in a desired position.

However, it has been found that such pivots are unsuitable for use in large and relatively heavy devices such as sun canopies whose housing is secured between fairly robust suspension members since then due to its weight, the housing tends to move from its set position; the housing cannot be put in a given position to a sufficient reproducible extent.

SUMMARY OF THE INVENTION

It is an object of the invention to provide an irradiation device with a housing which a user can easily and reliably fix in a desired position.

According to the invention an irradiation device having a housing accommodating at least one radiation source, which housing is pivotably secured to suspension members on two sides located substantially opposite each other and which housing can be fixed in given positions with respect to the suspension members, is characterized in that each pivot is composed of two co-operating concentric rings secured to the housing and to the suspension member, respectively, the facing walls of the rings being provided with series of regularly spaced co-operating projections and recesses, at least one of the rings being slightly deformable in the radial direction.

The irradiation device according to the invention has the advantage that a housing having a comparatively heavy weight (such as a housing of a sun (a nop) of a solarium in which a number of parallel tubular low-pressure mercury vapour discharge lamps emitting predominantly UV-A radiation is present) can be step-wise adjusted easily into given positions with respect to the suspension members by a user.

Each projection is pressed into a subsequent recess during rotation. The projection is slightly pressed away between two adjacent recesses because one of the rings is deformable in the radial direction. The rings preferably consist of a synthetic material.

In a practical embodiment the projections are present on the outer circumference of the inner ring and the recesses are present in the inner wall of the outer ring.

The projections are preferably located on wings which are deformable in the radial direction and which extend along the outer circumference of the inner ring. Due to the presence of the said wings the projections can easily be pressed from the recesses during rotation, enabling a user to adjust the housing into a subsequent position.

In a special embodiment of the irradiation device according to the invention the inner ring has a pair of further projections located substantially diametrically opposite each other in a plane which with respect to the plane of the co-operating projections and recesses is displaced in the axial direction, these further projections co-operating with abutment elements on the inner wall of the outer ring, thus determining the angle of rotation of the inner ring with respect to the outer ring.

The said pair of projections and the abutment elements create a limit upon rotation of the housing thus preventing it from being rotated through a too large angle with respect to the suspension members.

The invention may be used in irradiation devices for general purposes such as irradiation devices emitting both infrared and ultraviolet radiation. The invention can be used to particular advantage in a sun canopy of a solarium in which the sun canopy accommodates a number of parallel tubular low-pressure mercury vapour discharge lamps emitting predominantly UV-A radiation.

BRIEF DESCRIPTION OF THE DRAWINGS

The invention will be further described by way of example with reference to the accompanying drawings in which.

DETAILED DESCRIPTION OF THE PREFERRED EMBODIMENTS

Figure 1:
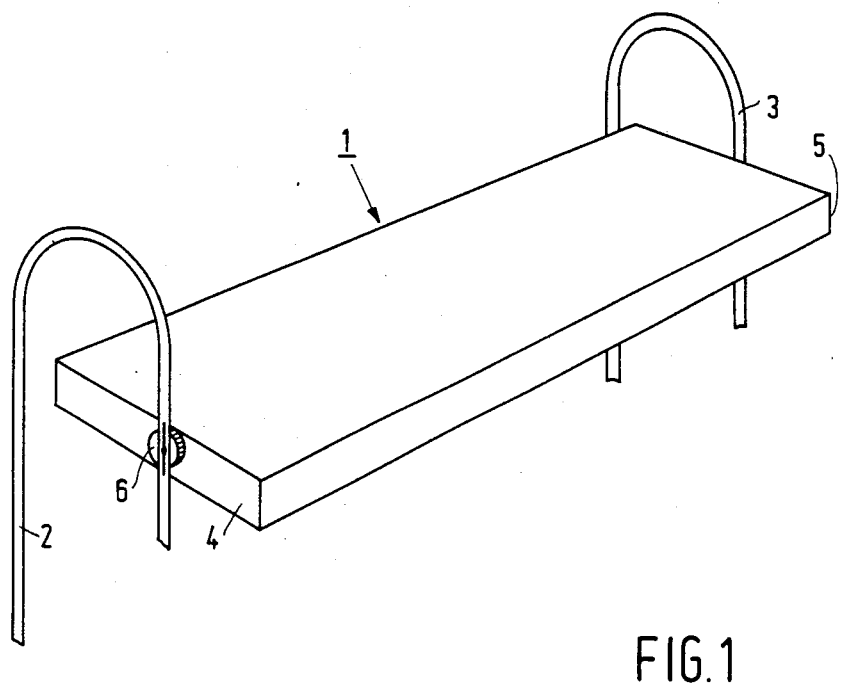
FIG. 1 shows an embodiment of an irradiation device according to the invention.

The irradiation device of FIG. 1 is a sun canopy and has an elongated rectangular housing 1 accommodating eight tubular low-pressure mercury vapour discharge lamps arranged parallel to each other. During operation these lamps emit predominantly UV-A radiation. Such radiation is used for tanning the human skin with substantially no erythema occurring. The housing is secured by means of pivots on its two short sides 4 and 5 to suspension members 2 and 3 forming part of a stand. Only one pivot, indicated by the reference numeral 6, is visible in the drawing. The position of the housing on the suspension members 2 and 3 is adjustable in height. The two suspension members are secured to a base which is not shown in the drawing.

Figure 3:
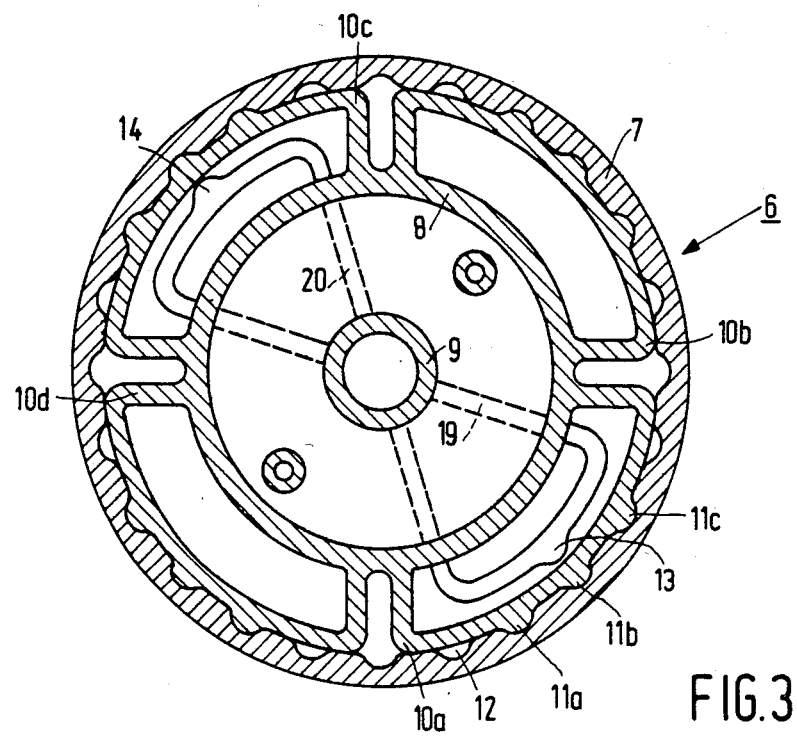
FIG. 3 is a cross-section of the pivot of FIG. 2 taken on the plane III—III.

The pivot is composed of two co-operating concentric synthetic material rings (see FIG. 3). The outer ring 7 is secured to a suspension member 2. The inner ring 8 is connected to the short side 4 of the housing by screws 1. The two rings 7 and 8 are secured together by means of a bolt in hub 9. The inner ring is provided on its outer circumference with four synthetic material wings 10a, 10b, 10c and 10d which are resiliently deformable in the radial direction and have projections on their outer sides. A number of these projections are indicated by 11a, 11b and 11c (on wing 10a). The projections constitute a series of three on each wing. The mutual distance between projection 11a and projection 11b is the same as that between 11b and 11c. Series of three projections are also present on the other wings 10b, 10c and 10d, these projections being similarly spaced from one another. The projections co-operate with recesses (such as 12) which are accommodated in the inner wall of ring 7. The distance between the recesses is equal to that between the projections. By rotating ring 8 with respect to ring 7 (thus when rotating the housing 1 with respect to the suspension members 2 and 3) the projections with the wings are initially slightly depressed by the wall parts between adjacent recesses, Finally the projections engage with the recesses, creating a fixed position. Thus a user can place the housing in a fixed position through a large number of angles with respect to the suspension members. In the construction shown in the drawing this is the case at every 15°, there being 24 recesses in the outer ring.

Figure 2:
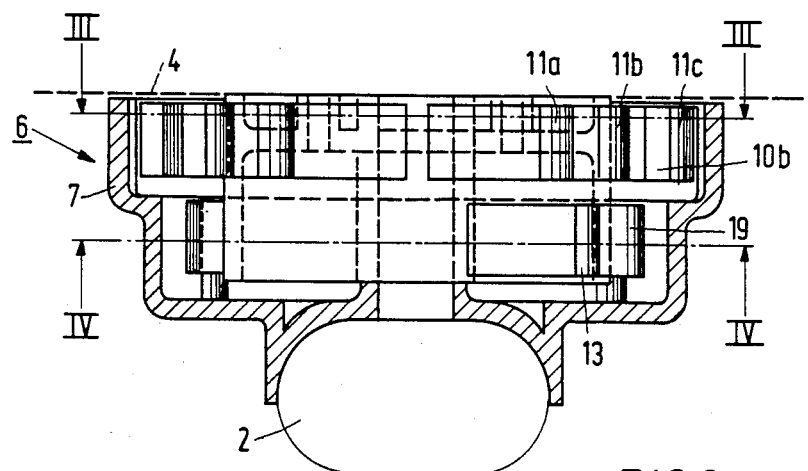
FIG. 2 shows the pivot of the device of FIG. 1, partly in an elevational view, partly in a cross-section.
Figure 4:
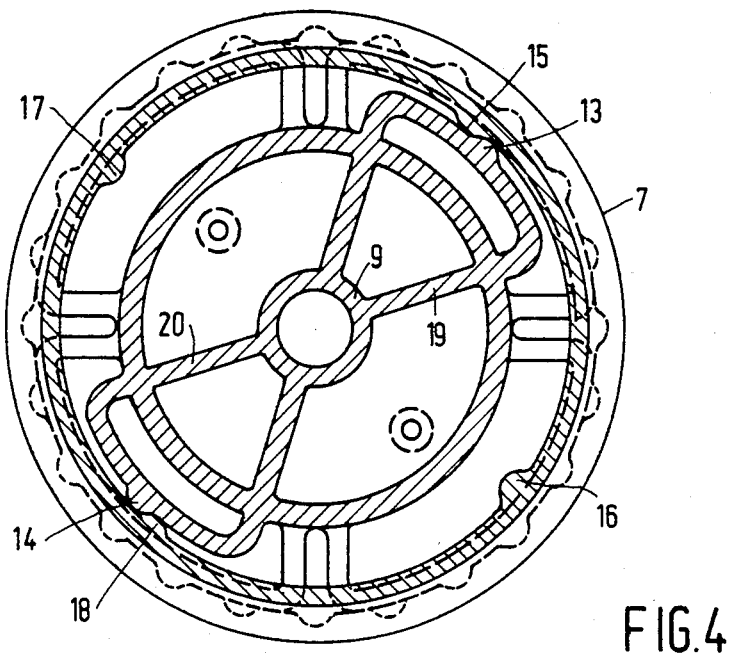
FIG. 4 is a cross-section of said pivot taken on the plane IV—IV.

The inner ring is also provided with two further second) projections 13 and 14 which are located substantially diametically opposite each other in a plane which is displaced in the axial direction (see FIG. 2) with respect to the plane of the projections and recesses (11a, 11b, 11c and 12, respectively). Projection 13 co-operates with abutment elements 15 and 16 and projection 14 communicates with abutment elements 17 and 18 (see FIG. 4)on the inner wall of the outer ring 7 so that the angle of possible rotation of the inner ring 8 is limited. The projections 13 and 14 are also slightly deformable in the radial direction. They are located on synthetic material wings (19 and 20), see FIG. 4. Rotation of projection 14 is bounded between the extreme positions determined by the elements 17 and 18. The inner ring 8 is rotatable within the angle of rotation of approximately 90° thus formed. The housing 1 is then rotatable to a bounded extent around a given main position (for example, the horizontal position). For a position different from the main position the projections 13 and 14 can be pushed with force over the abutment elements so that they are bounded between other abutment elements. This actually means that the housing 1 can be fixed in a number of positions around a different basic position (for example, the vertical position).

What is claimed is:

1. An irradiation device having a housing accommodating at least one radiation source, which housing is pivotably secured to suspension members on two sides located substantially opposite each other, and which housing can be fixed in given positions with respect to the suspension members, characterized in that each pivot is composed of two co-operating concentric rings secured to the housing and to the suspension member, respectively, the facing walls of the rings being provided with series of regularly spaced co-operating projections and recesses, at least one of the rings being slightly deformable in the radial direction.

2. An irradiation device as claimed in claim 1, characterized in that the projections are located on wings which are deformable in the radial direction and which extend along the outer circumference of the inner ring.

3. An irradiation device as claimed in claim 1 or 2, characterized in that the inner ring has a pair of further projections located substantially diametrically opposite each other in a plane which with respect to the plane of the co-operating projections and recesses is displaced in the axial direction, these further projections co-operating with abutment elements on the inner wall of the outer ring, thus determining the angle of rotation of the inner ring with respect to the outer ring.

* * * * *